(12) United States Patent
Hailand et al.

(10) Patent No.: US 8,314,162 B2
(45) Date of Patent: Nov. 20, 2012

(54) INITIATOR SYSTEM CONTAINING A DIARYLALKYLAMINE DERIVATE, HARDENABLE COMPOSITION AND USE THEREOF

(75) Inventors: Bettina Hailand, Herrsching a Ammersee (DE); Adrian S. Eckert, Herrsching (DE); Karsten Dede, Landsberg (DE)

(73) Assignee: 3M Innovative Properties Company, Saint Paul, MN (US)

( * ) Notice: Subject to any disclaimer, the term of this patent is extended or adjusted under 35 U.S.C. 154(b) by 25 days.

(21) Appl. No.: 12/996,906

(22) PCT Filed: May 28, 2009

(86) PCT No.: PCT/US2009/045377
§ 371 (c)(1),
(2), (4) Date: Dec. 8, 2010

(87) PCT Pub. No.: WO2009/151957
PCT Pub. Date: Dec. 17, 2009

(65) Prior Publication Data
US 2011/0077361 A1    Mar. 31, 2011

(30) Foreign Application Priority Data

Jun. 10, 2008  (EP) .................................... 08157904

(51) Int. Cl.
| | |
|---|---|
| C08L 63/00 | (2006.01) |
| C08L 69/00 | (2006.01) |
| C08L 71/00 | (2006.01) |
| C08J 3/28 | (2006.01) |
| C08F 2/50 | (2006.01) |
| A61K 6/00 | (2006.01) |
| C09D 11/00 | (2006.01) |

(52) U.S. Cl. ............. 522/14; 522/25; 522/28; 522/168; 522/170; 522/181; 522/182; 523/116; 523/117; 523/118

(58) Field of Classification Search .................... 522/25, 522/10, 28, 48, 14, 170, 181, 168, 182; 523/116–118
See application file for complete search history.

(56) References Cited

U.S. PATENT DOCUMENTS

| | | | |
|---|---|---|---|
| 3,018,262 A | 1/1962 | Schroeder |
| 3,117,099 A | 1/1964 | Proops |
| 3,729,313 A | 4/1973 | Smith |
| 3,741,769 A | 6/1973 | Smith |
| 3,808,006 A | 4/1974 | Smith |
| 4,250,053 A | 2/1981 | Smith |
| 4,256,828 A | 3/1981 | Smith |
| 4,394,403 A | 7/1983 | Smith |
| 4,642,126 A | 2/1987 | Zador |
| 4,652,274 A | 3/1987 | Boettcher |
| 4,835,193 A | 5/1989 | Hayase |
| 5,332,429 A | 7/1994 | Mitra |
| 5,545,676 A | 8/1996 | Palazzotto |
| 5,624,260 A | 4/1997 | Wilcox |
| 5,865,803 A | 2/1999 | Major |
| 5,893,714 A | 4/1999 | Arnold |
| 5,918,772 A | 7/1999 | Keller |
| 5,944,419 A | 8/1999 | Streiff |
| 5,998,495 A | 12/1999 | Oxman |
| 6,025,406 A | 2/2000 | Oxman |
| 6,043,295 A | 3/2000 | Oxman |
| 6,084,004 A | 7/2000 | Weinmann |
| 6,187,833 B1 | 2/2001 | Oxman |
| 6,245,828 B1 | 6/2001 | Weinmann |
| 6,315,566 B1 | 11/2001 | Shen |
| 6,572,693 B1 | 6/2003 | Wu |
| 6,624,211 B2 | 9/2003 | Karim |
| 6,765,036 B2 | 7/2004 | Dede |
| 6,899,948 B2 | 5/2005 | Zhang |
| 6,964,985 B2 | 11/2005 | Karim |
| 2006/0187752 A1 | 8/2006 | Keller |
| 2006/0270751 A1 | 11/2006 | Thalacker |
| 2007/0090079 A1 | 4/2007 | Kelller |
| 2007/0172789 A1 | 7/2007 | Muller |

FOREIGN PATENT DOCUMENTS

| | | |
|---|---|---|
| EP | 1340472 | 9/2003 |
| EP | 1498098 | 1/2005 |
| WO | WO 95/14716 | 6/1995 |
| WO | WO 00/69395 | 11/2000 |
| WO | WO 01/51540 | 7/2001 |
| WO | WO 03/059295 | 7/2003 |
| WO | WO 2005/051332 | 6/2005 |

OTHER PUBLICATIONS

Bi, A Visible Light Initiating System for Free Radical Promoted Cationic Polymerization, Macromolecules, vol. 27, No. 14, pp. 3683-3693, (Jul. 4, 1994).
Din En ISO 4049, "Dentistry—Polymer-Based Filling, Restorative and Luting Materials", Jan. 2001, pp. 1-29.
ISO 9917-1, "Dentistry—Water-Based Cements—Part 1: Powder/Liquid Acid-Base Cements", Nov. 1, 2003, pp. 1-22.
Marshall, A Silver-Free Single-Sheet Imaging Medium Based on Acid Amplification, Science, vol. 297, pp. 1516-1521, (2002).
Intl Search Report for Intl Appln. No. PCT/US2009/045377, 3 pages.

Primary Examiner — Susan W Berman
(74) Attorney, Agent, or Firm — Carlos M. Tellez

(57) ABSTRACT

The invention relates to an initiator system comprising a diarylalkylamine compound and a sensitizing agent. The invention also relates to a hardenable composition comprising the initiator system. The invention further relates to the use of the initiator system for initiating the hardening process of a hardenable composition being selected from cationically curing composition(s) and/or radically curing composition(s) or a mixture thereof. The initiator system and the hardening composition can be used in various fields, including the dental and orthodontic area.

15 Claims, No Drawings

INITIATOR SYSTEM CONTAINING A DIARYLALKYLAMINE DERIVATE, HARDENABLE COMPOSITION AND USE THEREOF

CROSS REFERENCE TO RELATED APPLICATIONS

This application is a national stage filing under 35 U.S.C. 371 of PCT/US2009/045377, filed May 28, 2009, which claims priority to European Patent Application No. 08157904.7, filed Jun. 10, 2008, the disclosure of which is incorporated by reference in its/their entirety herein.

FIELD OF THE INVENTION

In general, this invention relates to an initiator system for hardenable resins. More specifically, this invention relates to a hardenable composition containing a radically and/or a cationically hardenable material and an initiator system that is activated upon exposure to actinic radiation. The initiator system comprises a diarylalkyl amine derivative.

The invention also relates to the use of the initiator system and the hardenable composition in various fields including the dental and orthodontic area. The initiator system as well as the hardenable composition comprising the initiator system can be used in various fields, including the dental and orthodontic area, e.g. as a dental composition.

BACKGROUND ART

Radically curing compositions are typically cured by using binary and ternary initiator system. Especially for visible light radically curing compositions either a binary photoinitiator system consisting of a sensitizer (e.g. camphorquinone (CQ)) and an amine compound (e.g. ethyl 4-dimethylaminobenzoat (EDMAB)) or a ternary photoinitiator system consisting of a sensitizer (e.g. CQ), a so-called electron donor (e.g. EDMAB), and an iodonium salt (i.e. diphenyliodonium hexafluorostibonate) can be used. Both types of photoinitiator systems are common in radically curing dental compositions and often aniline derivatives are used as amine compounds.

Especially for visible light cationically curing compositions a ternary photoinitiator system consisting of a sensitizer (e.g. a 1,2-diketone like e.g. camphorquinone), a so-called electron donor (e.g. polycyclic aromatic compounds like e.g. anthracene and/or derivatives thereof), and an acid generator (i.e. a latent Lewis and/or Broensted acid like e.g. an iodonium salt as proton generator) is used. Such systems are described e.g. in WO 03/059295 and WO 05/051332.

Similarly, Smith, U.S. Pat. No. 4,256,828, describes photopolymerizable compositions that contain epoxides, an organic compound with hydroxyl functionality, and a photosensitive aromatic sulfonium or iodonium salt of a halogen containing complex ion.

Hayase et al., U.S. Pat. No. 4,835,193, describe photopolymerizable epoxy resin compositions that comprise an epoxy resin and a heteropoly-acid aromatic sulfonium salt as the photocuring catalyst.

In WO 95/14716 Neckers et al. describe photohardenable compositions that comprise a cationically polymerizable compound, a xanthene or fluorone dye, a hydrogen donor, and an onium salt.

Palazzotto et al., U.S. Pat. No. 5,545,676, describe addition polymerization of free-radically polymerizable materials. The disclosed photoinitiator system comprises an aryliodonium salt, a sensitizer, and an electron donor having an oxidation potential less than or equal to that of p-dimethoxybenzene.

Oxman et al., U.S. Pat. No. 6,025,406, U.S. Pat. No. 6,043,295, U.S. Pat. No. 5,998,495 and U.S. Pat. No. 6,187,833 describe a ternary photoinitiator system for curing of epoxy resins.

Weinmann et al., U.S. Pat. No. 6,084,004, describe compositions that undergo cationic curing and comprise a diaryliodonium compound, an alpha-dicarbonyl compound, a compound containing epoxide and/or oxetane groups, and an aromatic amine.

SUMMARY OF THE INVENTION

However, there is still a need for an improved curing system, which can be used for hardening cationically curing and/or radically curing compositions. There is also a need for a system enabling the practitioner to provide a composition with good aesthetics and sufficient mechanical properties.

In one embodiment, the invention is directed to an initiatorsystem comprising a diarylalkylamine compound as component A1 and a sensitizing agent as component A2.

Another embodiment of the invention is directed to a hardenable composition comprising
  the initiatorsystems as described in the text of the invention and
  a hardenable material as component B.

Moreover, the invention features the use of the initiatorsystem according to the invention for initiating the hardening process of a hardenable composition being selected from a cationically curing composition(s) and/or a radically curing composition(s) or mixtures thereof.

The invention is also directed to a method for curing a polymerizable resin comprising the steps of:
  providing a polymerizable composition as described in the text of the present invention and
  exposing the polymerizable composition to a light source having a wavelength and intensity to which the photoinitiator system being present in the polymerizable composition is reactive.

DEFINITIONS

Within the description of the invention, the following terms are defined as follows:

The term "visible light" is used to refer to light having a wavelength of about 400 to about 1000 nanometers (nm).

A "dental composition" is any composition which can be used in the dental field. In this respect the composition should be not detrimental to the patients' health and thus free of hazardous and toxic components being able to migrate out of the composition. Examples of dental compositions include permanent and temporary crown and bridge materials, artificial crowns, anterior or posterior filling materials, adhesives, mill blanks, lab materials and orthodontic devices.

A "monomer" is any chemical substance which can be characterized by a chemical formula, bearing polymerizable groups (including (meth)acrylate groups) which can be polymerized to oligomers or polymers thereby increasing the molecular weight. The molecular weight of monomers can usually simply be calculated based on the chemical formula given.

A "hardenable compound or material" is any compound which can be cured or solidified e.g. by heating to cause polymerization, chemical crosslinking, radiation-induced polymerization or crosslinking or using a redox initiator. A hardenable compound may contain only one, two, three or more polymerizable groups. Typical examples of polymerizable groups include epoxy groups and unsaturated carbon groups, such as a vinyl group being present i.a. in a (methyl) acrylate group.

A "resin" contains all hardenable compounds (monomers, oligomers and/or polymers) being present in the hardenable composition. The resin may contain only one hardenable compound or a mixture of different hardenable compounds.

A "filler" contains all fillers being present in the hardenable composition. Only one type of filler or a mixture of different fillers can be used.

"Dispersed within the resin" means that filler particles are present in the resin as discrete, unassociated (i.e. non-agglomerated and non-aggregated) particles.

A "nano-sized filler" is a filler, the individual particles thereof have a size in the region of nanometers, e.g. an average particle diameter of less than about 200 nm. Useful examples are given in U.S. Pat. No. 6,899,948 and U.S. Pat. No. 6,572,693, the content of which especially with regard to nano-sized silica particles is herein incorporated by reference.

An "initiator or initiator system" is a substance being able to start the curing process of a hardenable compound.

A "curing, hardening or setting reaction" is used interchangeable and refers to a reaction wherein physical properties such as viscosity and hardness of a composition changes over the time due to a chemical reaction between the individual components.

A "derivative" is a chemical compound showing a chemical structure closely related to the corresponding reference compound and containing all featured structural elements of the corresponding reference compound but having small modifications like bearing in addition comparably small additional chemical groups like e.g. $CH_3$, Br, Cl, or F or not bearing comparably small chemical groups like e.g. $CH_3$ in comparison to the corresponding reference compound. The following examples might illustrate this: tetramethyl bis-phenol A bearing four additional methyl groups with respect to the reference compound bis-phenol A, and bis-phenol F not bearing two additional methyl groups with respect to the reference compound bis-phenol A are derivatives of bis-phenol A within the meaning of this definition.

"Ambient conditions" mean the conditions which the inventive composition is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions are adjusted to about 23° C. and about 1013 mbar. In the dental and orthodontic field ambient conditions are reasonably understood as a pressure of about 950 to about 1050 mbar, temperature of about 15 to about 40° C. and relative humidity of about 20 to about 80%.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Unless otherwise indicated, all numbers expressing quantities of ingredients, measurement of properties such as contrast ratio and so forth used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

DETAILED DESCRIPTION OF THE INVENTION

It has been found that diaryl alkyl amine derivatives comprising no or only a limited number of alkyl groups attached onto either or both of the aryl substituents, but typically no alkoxy groups attached onto the aryl substituents are suitable electron donors in various applications, especially for radically and/or cationically curing compositions.

These derivatives can be used e.g. as an alternative to aniline structure containing derivatives like e.g. EDMAB for radically curing compositions as well as an alternative to polycyclic aromatic electron donors like e.g. anthracene and its derivatives like 2-Ethyl-9,10-dimethoxy-anthracene (EDMO) for cationically curing compositions.

Moreover, it was found that compositions comprising the inventive initiator system often show comparable, sometimes even improved mechanical properties compared to the corresponding compositions comprising anthracene derived electron donors.

One feature, which might contribute to the aesthetics of a dental composition, is the fluorescence. Whereas a slight fluorescence is sometimes desirable, a heavy fluorescence is often unwanted. In contrast to aniline and anthracene derived electron donors, the diarylalkyl amine components of the present invention do not show an undesired fluorescence.

Thus, the present invention features a new class of initiator components for binary and ternary initiator systems especially suitable for hardening radically and/or cationically curing compositions, including dental compositions.

The inventive initiator system is typically a photoinitiator system.

Thus, certain embodiments of the inventive hardenable compositions may provide a very useful combination of features like polymerization speed, polymerization depth, and/or shelf life.

The enhancement in the cure speed and cure depth which may be realized by this invention may allow a dentist to prepare and cure larger restorations at one time, thereby saving time and effort.

The reduction in unwanted fluorescence can also make matching the restorative to various tooth shades easier and more accurate.

Certain embodiments the inventive hardenable composition can be characterized by at least one of the following features after hardening:
Compressive strength (MPa): at least about 300 or at least about 310 or at least about 320 or at least about 330, determined according to ISO 9917 using cubic specimen (dimensions 3 mm×3 mm×5 mm),
Flexural strength (MPa): at least about 100 or at least about 110 or at least about 120 determined according to ISO 4049, E-modulus (GPa): at least about 8 or at least about 9 or at least about 10 determined according to ISO 4049, Bonded disk shrinkage-strain (vol.-%): less or equal than about 1.1 or less or equal than about 1.0 or less or equal than about 0.9 determined according to the Watts protocol, Depth of cure (measured values of depth of cure in a metal mold according to ISO 4049), at least about 2.10 mm, Depth of cure (measured values of depth of cure in a delrin mold according to ISO 4049), at least about 3.50 mm, Lack of intense fluorescence (determined as described in the example section) e.g., in a wavelength range of about 370 nm to about 650 nm, the composition being irradiated with monochromatic radiation of about 355 nm wavelength at 23° C. The composition typically does show not more than about 70% or not more than about 50% or not more than about 30% or not more than about 20% fluorescence compared to a composition containing EDMO instead of the inventive diarylalkylamine compound.

For certain embodiments (e.g. dental composite materials), a combination of the following parameters can be preferred:

E.g. for a radically curing composition a combination of appropriate mechanical properties (e.g. compressive strength, flexural strength, depth of cure, abrasion, shrinkage and/or E-Modulus) and lack of intense fluorescence can be preferred.

E.g. for a cationically curing composition the combination of appropriate values for Bonded Disk Shrinkage Strain and Two Body Wear Resistance according to ACTA and lack of intense fluorescence can be preferred.

The first component in the initiator system is a diaryl alkyl amine compound or derivative acting typically as an electron donor compound.

A wide variety of electron donor compounds can be employed in the practice of the invention, and generally are capable of increasing the speed of polymerization and/or the depth of polymerization of a composition according to the invention when exposed to visible light of the desired wavelength, as compared to the same composition but excluding the electron donor compound.

The electron donor compound according to the invention comprises a diaryl alkyl amine structure, wherein one or both aryl substituents of the diary alkyl amine may comprise alkyl groups (including C1 to C8 or C1 to C6 or C1 to C4) but typically no alkoxy groups.

In a preferred embodiment, the alkyl substituents, if present, are independently selected from methyl groups, ethyl group, propyl groups or tert-butyl groups, preferably tert-butyl groups. The aryl substituents do typically not comprise alkoxy groups like e.g. methoxy or ethoxy groups, being directly attached onto the aryl structure.

Some electron donor compounds for use in the invention typically possess one or more of the following properties:

(a) they are soluble in a polymerizable or hardenable composition;

(b) they do not absorb a significant amount of light at the wavelength of the light used to photopolymerize the composition, typically the wavelength at which the visible light sensitizer exhibits maximum absorption, by which it is meant that the electron donor compound does not detrimentally affect the performance of the visible light sensitizer;

(c) they have an oxidation potential ($E_{ox}$) greater than 0 but less than that of 1,4-dimethoxybenzene when measured versus a saturated calomel electrode (SCE);

(d) they yield a photoinitiator system that has a photoinduced potential less than that of 3-dimethylaminobenzoic acid in a standard solution of $2.9 \times 10^{-5}$ moles/g diphenyl iodonium hexafluoroantimonate and $1.5 \times 10^{-5}$ moles/g camphorquinone in 2-butanone;

(e) a $pk_b$ greater than 8;

(g) they impart not more than a minimal amount of objectionable fluorescence to the polymerized resin; and (h) they can be used in a lower effective concentration than other polymerization aids.

Other factors that may influence the selection of the electron donor compound for a particular composition include the chemical nature of the polymerizable resin chosen and its shelf stability.

More specifically, electron donor compounds with the following structure may be employed: $Ar^1Ar^2RN$, with $Ar^1$ and $Ar^2$ being independently selected from phenyl or alkyl (including C1 to C8 or C1 to C6 or C1 to C4) substituted phenyl, R being an alkyl group (including C1 to C8 or C1 to C5 or C1 to C3; wherein one or more H atoms can be substituted by halogen, e.g. Cl, Br, I) and N being nitrogen.

More specifically, according to a preferred embodiment the electron donor compound of the invention can be characterized by at least one of the following features:

The aryl substitutent(s) bear not more than about four or three or two alkyl (e.g. C1 to C8) groups, preferably not more than about 2 tert-butyl groups.

The aryl substitutent(s) do not contain alkoxy groups directly attached onto the aryl structure. The presence of alkoxy groups might negatively influence the reactivity of the initiator system and sometime also negatively affects the aesthetics of the hardened composition.

The aryl substitutent(s) do typically also not contain halogen atoms directly attached on the aryl structure.

The diaryl alkyl amine derivative has a molecular weight in the range of about 150 to about 400 or about 180 to about 350.

Specific examples of diaryl alkyl amine derivative which can be used have the following structures:

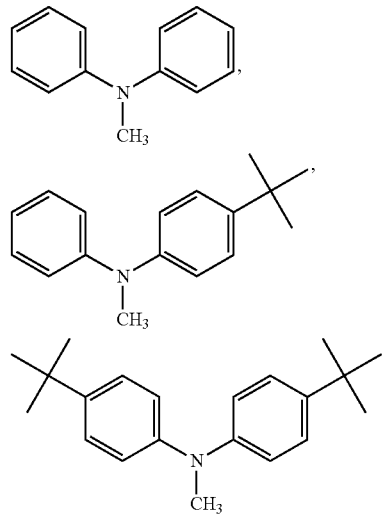

Combinations of either of these derivatives can be used, if desired.

For radically curing compositions it has been found that in contrast to aniline derivatives, the inventive diaryl alkyl amine components show similar initiator properties like these aniline derivatives (e.g. EDMAB) e.g. in terms of comparable mechanical properties of the cured composition (shown e.g. by compressive strength, flexural strength and/or E-Modulus); and/or comparable volume shrinkage during curing of the composition (shown e.g. by measured values of Watts bonded disk shrinkage strain relative to each other);

but less fluorescence.

For cationically curing compositions it has been found that in contrast to aniline derivatives as well as in contrast to N,N,N-triphenylamine derivatives, as well as in contrast to polycyclic aromatic donors the inventive diaryl alkyl amine components show similar initiator properties like polycyclic aromatic donors (e.g. anthracene, EDMO) e.g. in terms of comparable wear resistance of the cured composition (shown e.g. by measured values of ACTA wear resistance test relative to each other);

comparable volume shrinkage during curing of the composition (shown e.g. by measured values of Watts bonded disk shrinkage strain relative to each other); and/or comparable depth of cure (shown e.g. by measured values of depth of cure in preferably a metal mold according to ISO 4049 relative to each other);

but less fluorescence.

The diaryl alkyl amine derivative can be present at about 0.01 to about 5 wt.-%, or about 0.02 to about 3 wt.-% or about 0.05 to about 1 wt.-% with respect to the weight of the whole composition.

The second component in the initiator system is a sensitizing agent, including visible light sensitizers. The light sensitizer should be partly or fully soluble in the photopolymerizable composition, free of functionalities that would substantially interfere with the cationic polymerization process, and capable of light absorption somewhere within the range of wavelengths between about 400 and about 1000 nanometers (nm). Preferred visible light sensitizers contain one or more carbonyl functional groups.

Suitable visible light sensitizers may include compounds in the following categories: ketones, coumarin dyes (e.g., ketocoumarins), xanthene dyes, fluorone dyes, fluorescein dyes, aminoketone dyes, and p-substituted aminostyryl ketone compounds. Ketones (e.g., monoketones or alpha-diketones), coumarin dyes (e.g., ketocoumarins), xanthene dyes, fluorone dyes, and fluorescein dyes are particularly preferred visible light sensitizers for use in the invention. For applications requiring deep cure (e.g., cure of highly-filled composites), it is preferred to employ sensitizers having an extinction coefficient below about 1000 lmole$^{-1}$cm$^{-1}$, more preferably about or below 100 lmole$^{-1}$cm$^{-1}$, at the desired wavelength of irradiation for photopolymerization. The alpha-diketones are an example of a class of visible light sensitizers having this property, and are particularly preferred for dental applications.

By way of example, a preferred class of ketone visible light sensitizers has the formula:

where X is CO or CR$^1$R$^2$ where R$^1$ and R$^2$ can be the same or different, and can be hydrogen, alkyl, alkaryl or aralkyl, b is zero, and A and B can be the same or different and can be substituted (having one or more non-interfering substituents) or unsubstituted aryl, alkyl, alkaryl, or aralkyl groups, or together A and B can form a cyclic structure which can be a substituted or unsubstituted cycloaliphatic, aromatic, heteroaromatic or fused aromatic ring.

Suitable ketones of the above formula include monoketones (b=0) such as 2,2-, 4,4- or 2,4-dihydroxybenzophenone, di-2-pyridyl ketone, di-2-furanyl ketone, di-2-thiophenyl ketone, benzoin, fluorenone, chalcone, Michler's ketone, 2-fluoro-9-fluorenone, 2-chlorothioxanthone, acetophenone, benzophenone, 1- or 2-acetonaphthone, 9-acetylanthracene, 2-, 3- or 9-acetylphenanthrene, 4-acetylbiphenyl, propiophenone, n-butyrophenone, valerophenone, 2-, 3- or 4-acetylpyridine, 3-acetylcoumarin and the like. Suitable diketones include aralkyldiketones such as anthraquinone, phenanthrenequinone, o-, m- and p-diacetylbenzene, 1,3-, 1,4-, 1,5-, 1,6-, 1,7- and 1,8-diacetylnaphthalene, 1,5-, 1,8- and 9,10-diacetylanthracene, and the like. Suitable I-diketones (b=1 and x=CO) include 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'-3 3'- and 4,4'-dihydroxylbenzil, furil, di-3,3'-indolylethanedione, 2,3-bornanedione(camphorquinone), biacetyl, 1,2-cyclohexanedione, 1,2-naphthaquinone, acenaphthaquinone, 1-phenyl-1,2-propanedione, and the like.

Examples of particularly preferred visible light sensitizers include the alpha-diketones: camphorquinone; glyoxal; biacetyl; 3,3,6,6-tetramethylcyclohexanedione; 3,3,7,7-tetramethyl-1,2-cycloheptanedione; 3,3,8,8-tetramethyl-1,2-cyclooctanedione; 3,3,18,18-tetramethyl-1,2-cyclooctadecanedione; dipivaloyl; benzil; furil; hydroxybenzil; 2,3-butanedione; 2,3-pentanedione; 2,3-hexanedione; 3,4-hexanedione; 2,3-heptanedione; 3,4-heptanedione; 2,3-octanedione; 4,5-octanedione; 1,2-cyclohexanedione; and 1-phenyl-1,2-propanedione. Of these, camphorquinone is the most preferred visible light sensitizer.

Examples of preferred fluorone dyes include, but are not limited to, fluorescein, 4'5'-dibromofluorescein, erythrosin B, ethyl eosin, eosin Y, and erythrosin, yellowish blend.

Typically, the visible light sensitizer can be present at about 0.01 to about 5 wt.-% or about 0.05 to about 3 wt.-% or from about 0.1 to about 2 wt.-% based on the whole weight of the composition.

The iodonium salt, if present, should be soluble in the composition and preferably is shelf-stable, meaning it does not spontaneously promote polymerization when dissolved therein in the presence of the visible light sensitizer and the electron donor compound.

Accordingly, selection of a particular iodonium salt may depend to some extent upon the particular resin, visible light sensitizer and electron donor that are chosen. Suitable iodonium salts are described in U.S. Pat. Nos. 3,729,313, 3,741, 769, 3,808,006, 4,250,053 and 4,394,403. The iodonium salt can be a simple salt, containing an anion such as Cl$^-$, Br$^-$, I$^-$ or C$_2$H$_5$SO$_3$$^-$; or a metal complex salt containing an antimonate, arsenate, phosphate or borate such as SbF$_5$OH$^-$ or AsF$_6$$^-$. Mixtures of iodonium salts can be used if desired.

According to a preferred embodiment, the iodonium salt is a diaryl iodonium salt.

Examples of useful aromatic iodonium complex salt photoinitiators include: diphenyliodonium tetrafluoroborate; di(4-methylphenyl)iodonium tetrafluoroborate; phenyl-4-methylphenyliodonium tetrafluoroborate; di(4-heptylphenyl)iodonium tetrafluoroborate; di(3-nitrophenyl)iodonium hexafluorophosphate; di(4-chlorophenyl)iodonium hexafluorophosphate; di(naphthyl)iodonium tetrafluoroborate; di(4-trifluoromethylphenyl)iodonium tetrafluoroborate; diphenyliodonium hexafluorophosphate; di(4-methylphenyl)iodonium hexafluorophosphate; diphenyliodonium hexafluoroarsenate; di(4-phenoxyphenyl)iodonium tetrafluoroborate; phenyl-2-thienyliodonium hexafluorophosphate; 3,5-dimethylpyrazolyl-4-phenyliodonium hexafluorophosphate; diphenyliodonium hexafluoroantimonate; 2,2'-diphenyliodonium tetrafluoroborate; di(2,4-dichlorophenyl)

iodonium hexafluorophosphate; di(4-bromophenyl) iodonium hexafluorophosphate; di(4-methoxyphenyl) iodonium hexafluorophosphate; di(3-carboxyphenyl) iodonium hexafluorophosphate; di(3-methoxycarbonylphenyl)iodonium hexafluorophosphate; di(3-methoxysulfonylphenyl)iodonium hexafluorophosphate; di(4-acetamidophenyl)iodonium hexafluorophosphate; di(2-benzothienyl)iodonium hexafluorophosphate; and diphenyliodonium hexafluoroantimonate.

Of the aromatic iodonium complex salts which are suitable for use in the compositions of the invention diaryliodonium hexafluorophosphate, diaryliodonium hexafluoroantimonate, 4-octyloxyphenyl phenyliodonium hexafluoroantimonate, 4-(2-hydroxytetradecyloxyphenyl)phenyliodonium hexafluoroantimonate, and 4-(1-methylethyl)phenyl 4-methylphenyliodonium tetrakis(pentafluorophenyl)borate are among the preferred salts. These salts are preferred because, in general, they promote faster reaction, and are more soluble in inert organic solvents than are other aromatic iodonium salts of complex ions.

The aromatic iodonium complex salts may be prepared by metathesis of corresponding aromatic iodonium simple salts (such as, for example, diphenyliodonium bisulfate). Thus, for example, the complex salt diphenyliodonium tetrafluoroborate can be prepared by the addition at 60° C. of an aqueous solution containing 29.2 g silver fluoroborate, 2 g fluoroboric acid, and 0.5 g phosphorous acid in about 30 ml of water to a solution of 44 g (139 millimoles) of diphenyliodonium chloride. The silver halide that precipitates is filtered off and the filtrate concentrated to yield diphenyliodonium fluoroborate which may be purified by recrystallization.

The aromatic iodonium simple salts may be prepared by various methods including (1) coupling of two aromatic compounds with iodyl sulfate in sulfuric acid, (2) coupling of two aromatic compounds with an iodate in acetic acid-acetic anhydride-sulfuric acid, (3) coupling of two aromatic compounds with an iodine acetate in the presence of an acid, and (4) condensation of an iodoso compound, an iodoso diacetate, or an iodoxy compound with another aromatic compound in the presence of an acid. Diphenyliodonium bisulfate is prepared by method (3), for example, by the addition over a period of eight hours at below 5° C. of a mixture of 35 ml of conc. sulfuric acid and 50 ml of acetic anhydride to a well-stirred mixture of 55.5 ml of benzene, 50 ml of acetic anhydride, and 53.5 g of potassium iodate. The mixture is typically stirred for an additional four hours at 0°-5° C. and at room temperature (about 25° C.) for 48 hours and treated with 300 ml of diethyl ether. On concentration, crude diphenyliodonium bisulfate precipitates and may be purified by recrystallization if desired.

The iodonium salt, if present, can be present from about 0.05 to about 10 wt.-% or from about 0.1 to about 5 wt.-%, or from about 0.5 to about 3 wt.-%, based on the overall composition.

The invention is also directed to a hardenable composition comprising the inventive initiator system and a hardenable material.

The curable materials can either be cationically curing or radically curing or a combination thereof, with the proviso that if the hardenable composition is a radically curing composition, the initiator system comprises components A1 and A2, and if the hardenable composition is a cationically curing composition, the initiator system comprises in addition to components A1 and A2 an iodonium salt as component A3.

In one embodiment the hardenable material is a cationically polymerizable resin, which may be selected from epoxy, oxetane, vinyl ether and spiro-orthocarbonate resins, and combinations thereof. Preferably, the cationically polymerizable resin comprises an epoxy resin, especially a silicon-containing epoxy resin, or a blend of a silicon-containing epoxy resin and an epoxy resin that does not contain silicon.

Advantageously, the photopolymerizable compositions of the invention are sensitive throughout the visible light region and polymerize without appreciable application of heat. Photopolymerization of the compositions takes place upon exposure of the compositions to a source of actinic radiation having a wavelength within this spectral region.

The cationically polymerizable resins useful in the compositions of the invention include, for example, epoxy (including silicon-containing epoxy), oxetane, spiro-orthocarbonate, and, vinyl ether resins, as well as combinations thereof.

Useful epoxy resins are organic compounds having an oxirane ring, i.e., a group of the formula

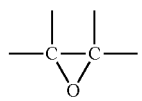

which is polymerizable by ring opening. Such materials, broadly called epoxides, include monomeric epoxy compounds and epoxides of the polymeric type and can be aliphatic, cycloaliphatic, aromatic or heterocyclic. These materials generally have, on the average, at least 1 polymerizable epoxy group per molecule, preferably at least about 1.5, and more preferably at least about 2 polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The epoxides may be pure compounds or may be mixtures of compounds containing one, two, or more epoxy groups per molecule. The "average" number of epoxy groups per molecule is determined by dividing the total number of epoxy groups in the epoxy resin by the total number of epoxy-containing molecules present.

These epoxy resins may vary from low molecular weight monomeric materials to high molecular weight polymers and may vary greatly in the nature of their backbone and substituent groups. For example, the backbone may be of any type and substituent groups thereon can be any group that does not substantially interfere with cationic polymerization at room temperature. Illustrative of permissible substituent groups are halogens, ester groups, ethers, sulfonate groups, siloxane groups, nitro groups, phosphate groups, and the like. The molecular weight of the epoxy resin may vary from about 58 to about 100,000 or more.

Particularly preferred epoxy resins include those which contain cyclohexene oxide groups such as epoxycyclohexanecarboxylates, typified by 3,4-epoxycyclohexylmethyl-3,4-epoxycyclohexanecarboxylate, 3,4-epoxy-2-methylcyclohexylmethyl-3,4-epoxy-2-methylcyclo-hexane carboxylate, and bis(3,4-epoxy-6-methylcyclohexylmethyl)adipate. For a more detailed list of useful epoxides of this nature, reference is made to U.S. Pat. Nos. 3,117,099 and 6,245,828. Other epoxy resins that are useful in the compositions of this invention include glycidyl ether monomers of the formula

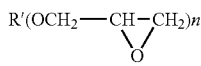

where R' is alkyl or aryl, and n is an integer of 1 to 6. Examples are glycidyl ethers of polyhydric phenols obtained by reacting a polyhydric phenol with an excess of chlorohydrin such as epichlorohydrin (e.g., the diglycidyl ether of 2,2-bis-(2,3-epoxypropoxyphenol)propane). Further examples of epoxides of this type are described in U.S. Pat. No. 3,018,262.

There is a host of commercially available epoxy resins that can be used in this invention. In particular, epoxides that are readily available include octadecylene oxide, epichlorohydrin, styrene oxide, vinyl cyclohexene oxide, glycidol, glycidylmethacrylate, diglycidyl ether of Bisphenol A (e.g., those available under the trade designations "Epon 828", "Epon 825", "Epon 1004" and "Epon 1010" from Shell Chemical Co., "DER-331", "DER-332", and "DER-334", from Dow Chemical Co.), vinylcyclohexene dioxide (e.g., "ERL-4206" from Union Carbide Corp.), 3,4-epoxycyclohexylmethyl-3,4-epoxycyclohexane carboxylate (e.g., "ERL-4221" or "CYRACURE UVR 6110" or UVR 6105" from Union Carbide Corp.), 3,4-epoxy-6-methylcyclohexyl-methyl-3,4-epoxy-6-methyl-cyclohexene carboxylate (e.g., "ERL-4201" from Union Carbide Corp.), bis(3,4-epoxy-6-methylcyclohexylmethyl)adipate (e.g., "ERL-4289" from Union Carbide Corp.), bis(2,3-epoxycyclopentyl)ether (e.g., "ERL-0400" from Union Carbide Corp.), aliphatic epoxy modified from polypropylene glycol (e.g., "ERL-4050" and "ERL-4052" from Union Carbide Corp.), dipentene dioxide (e.g., "ERL-4269" from Union Carbide Corp.), epoxidized polybutadiene (e.g., "Oxiron 2001" from FMC Corp.), silicone resin containing epoxy functionality, flame retardant epoxy resins (e.g., "DER-580", a brominated bisphenol type epoxy resin available from Dow Chemical Co.), 1,4-butanediol diglycidyl ether of phenolformaldehyde novolak (e.g., "DEN-431" and "DEN-438" from Dow Chemical Co.), and resorcinol diglycidyl ether (e.g., "Kopoxite" from Koppers Company, Inc.), bis(3,4-epoxycyclohexyl)adipate (e.g., "ERL-4299" or "UVR-6128", from Union Carbide Corp.), 2-(3,4-epoxycyclohexyl-5, 5-spiro-3,4-epoxy)cyclohexane-meta-dioxane (e.g., "ERL-4234" from Union Carbide Corp.), vinylcyclohexene monoxide 1,2-epoxyhexadecane (e.g., "UVR-6216" from Union Carbide Corp.), alkyl glycidyl ethers such as alkyl $C_8$-$C_{10}$ glycidyl ether (e.g., "HELOXY Modifier 7" from Shell Chemical Co.), alkyl $C_{12}$-$C_{14}$ glycidyl ether (e.g., "HELOXY Modifier 8" from Shell Chemical Co.), butyl glycidyl ether (e.g., "HELOXY Modifier 61" from Shell Chemical Co.), cresyl glycidyl ether (e.g., "HELOXY Modifier 62" from Shell Chemical Co.), p-tert-butylphenyl glycidyl ether (e.g., "HELOXY Modifier 65" from Shell Chemical Co.), polyfunctional glycidyl ethers such as diglycidyl ether of 1,4-butanediol (e.g., "HELOXY Modifier 67" from Shell Chemical Co.), diglycidyl ether of neopentyl glycol (e.g., "HELOXY Modifier 68" from Shell Chemical Co.), diglycidyl ether of cyclohexanedimethanol (e.g., "HELOXY Modifier 107" from Shell Chemical Co.), trimethylol ethane triglycidyl ether (e.g., "HELOXY Modifier 44" from Shell Chemical Co.), trimethylol propane triglycidyl ether (e.g., "HELOXY Modifier 48" from Shell Chemical Co.), polyglycidyl ether of an aliphatic polyol (e.g., "HELOXY Modifier 84" from Shell Chemical Co.), polyglycol diepoxide (e.g., "HELOXY Modifier 32" from Shell Chemical Co.), bisphenol F epoxides (e.g., "EPN-1138" or "GY-281" from Ciba-Geigy Corp.), 9,9-bis[4-(2,3-epoxypropoxy)-phenyl]fluorenone (e.g., "Epon 1079" from Shell Chemical Co.).

Still other useful epoxy resins contain copolymers of acrylic acid esters or glycidol such as glycidylacrylate and glycidylmethacrylate with one or more copolymerizable vinyl compounds. Examples of such copolymers are 1:1 styrene-glycidylmethacrylate, 1:1 methylmethacrylate-glycidylacrylate and a 62.5:24:13.5 methylmethacrylate-ethyl acrylate-glycidylmethacrylate.

Other useful epoxy resins include epichlorohydrins, alkylene oxides, e.g., propylene oxide, styrene oxide; alkenyl oxides, e.g., butadiene oxide; and glycidyl esters, e.g., ethyl glycidate.

Particulary preferred epoxides are those that contain silicon, useful examples of which are described in WO 01/51540, such as: 7-Oxabicyclo[4.1.0]heptane; 3,3',3''',3''''-[(2,4,6,8-tetramethylcyclotetrasiloxan-2,4,6,8-tetrayl)tetra-2,1-ethandiyl]tetrakis-; 7-Oxabicyclo[4.1.0]heptan, 3,3',3'',3''',3''''-[(2,4,6,8,10-pentamethylcyclopentasiloxan-2,4,6,8,10-pentayl)penta-2,1-ethandiyl]pentakis-, Silane; methylbis[2-(7-oxabicyclo[4.1.0]hept-3-yl)ethyl]phenyl-; Silane, dimethylbis[2-(7-oxabicyclo[4.1.0]hept-3-yl)methyl]-; Silane, dimethyl[2-(7-oxabicyclo[4.1.0]hept-3-yl)methyl][2-(7-oxabicyclo[4.1.0]hept-3-yl)ethyl]-; Silane, 1,4-phenylenbis[dimethyl[2-(7-oxabicyclo[4.1.0]hept-3-yl)ethyl]]-; Silane 1,2-ethylenbis[dimethyl[2-(7-oxabicyclo[4.1.0]hept-3-yl)ethyl]]-; Silane; dimethylbis[2-(7-oxabicyclo[4.1.0]hept-3-yl)ethyl]-; 1,3-Bis[2-(3,4-epoxycyclohexyl)ethyl]-1,1,3,3-tetramethyldisiloxane; Silane 2,5-bicyclo[2.2.1.]heptylenbis[dimethyl[2-(7-oxabicyclo[4.1.0]hept-3-yl) ethyl]]-; Silane 1,6-hexylenbis[dimethyl[2-(7-oxabicyclo[4.1.0]hept-3-yl)ethyl]]-; Silane 1,1',1''-(1,2,4-cyclohexylentris(dimethyl[2-(7-oxabicyclo[4.1.0]hept-3-yl)ethyl]))-; Trisiloxane, 3-[[dimethyl[2-(7-oxabicyclo[4.1.0]hept-3-yl)ethyl]silyl]oxy]-1,1,5,5-tetramethyl-1,5-bis[2-(7-oxabicyclo[4.1.0]hept-3-yl)ethyl]-3-phenyl-; Disiloxane 1,1',1''-(1,2,4-cyclohexanetriyltri-2,1-ethanediyl)tris[1,1,3,3-tetramethyl-3-[2-(7-oxabicyclo[4.1.0]hept-3-yl)ethyl]]-; Trisiloxane, 3,3-bis[[dimethyl[2-(7-oxabicyclo[4.1.0]hept-3-yl)ethyl]silyl]oxy]-1,1,5,5-tetramethyl-1,5-bis[2-(7-oxabicyclo[4.1.0]hept-3-yl)ethyl]-; Trisiloxane, 3-[[dimethyl[2-(7-oxabicyclo[4.1.0]hept-3-yl)ethyl]silyl]oxy]-1,1,3,5,5-pentamethyl-1,5-bis[2-(7-oxabicyclo[4.1.0]hept-3-yl) ethyl]-, 1,3,5,7-tetrakis(2,1-ethanediyl-3,4-epoxycyclohexyl)-1,3,5,7-tetramethylcyclo-tetrasiloxane and 1,3,5,7,9-pentakis(2,1-ethanediyl-3,4-epoxycyclohexyl)-1,3,5,7,9-pentamethylcyclopentasiloxane.

The cationically polymerizable resin may also be provided by a vinyl ether resin. Examples of vinyl ether resins that may be used include, but are not limited to, tri(ethylene glycol) divinyl ether (TEGDVE), glycidyl vinyl ether (GVE), butanediolvinyl ether (BDVE), di(ethylene glycol) divinyl ether (DEGDVE), 1,4-cyclohexanedimethdiol divinyl ether(CHDMDVE), 4-(isopropenyloxymethyl)-1,3-dioxolan-2-one (POMDO), 2-chloroethyl vinyl ether (CEVE), 2-ethylhexyl vinyl ether (EHVE), ethyl vinyl ether (EVE), n-propyl vinyl ether (NPVE), isopropyl vinyl ether (IPVE), n-butyl vinyl ether (NBVE), isobutyl vinyl ether (IBVE), octadecyl vinyl ether (ODVE), cyclohexyl vinyl ether (CVE), butanediol divinyl ether (BDDVE), hydroxybutyl vinyl ether (HBVE), cyclohexanedimethanol monovinyl ether (CHMVE), tert-butyl vinyl ether (TBVE), tert-amyl vinyl ether (TAVE), dodecyl vinyl ether (DDVE), ethylene glycol divinyl ether (EGDVE), ethylene glycol monovinyl ether (EGMVE), hexanediol divinyl ether (HDDVE), hexanediol monovinyl ether (HDMVE), diethylene glycol monovinyl ether (MVE-2), triethyleneglycol methyl vinyl ether (MTGVE), tetraethylene glycol divinyl ether (DVE-4), trimethylolpropane trivinyl ether (TMPTVE), aminopropyl vinyl ether (APVE), polytetrahydrofuran divinyl ether (PTHFDVE), n-butyl vinyl ether (n-BVE), 4-hydroxybutyl vinyl ether (HBVE), ethylene glycol butyl vinyl ether (EGBVE), 2-diethylamino ethyl vinyl ether (DEAEVE), dipropylene glycol divinyl ether (DPGDVE), a vinyl ether terminated aromatic ester monomer (e.g., hydroxybutyl vinyl ether isophthalate which can be purchased from Allied-Signal Inc., Engineered Materials Sector, Morristown, N.J. under the trademark VECTOMER 4010), a vinyl ether terminated aliphatic ester monomer (e.g., cyclohexane dimethanol monovinyl ether glutarate which can be purchased from Allied-Signal Inc. under the trademark VECTOMER 4020), a vinyl ether terminated aliphatic urethane oligomer (e.g., VECTOMER 2020 which can be purchased from Allied-Signal Inc.), and a vinyl ether terminated aromatic urethane oligomer (e.g., VECTOMER 2015 and VECTOMER 2010, both of which can be purchased from Allied-Signal Inc.

Blends of various cationically polymerizable resins are also contemplated in this invention. Examples of such blends include two or more weight average molecular weight distributions of resin-containing compounds, such as low molecular weight (below 200), intermediate molecular weight (about 200 to 10,000) and higher molecular weight (above about 10,000). Alternatively or additionally, the resin may contain a blend of resin-containing materials having different chemical natures, such as aliphatic and aromatic, or functionalities, such as polar and non-polar. Other cationically polymerizable polymers may additionally be incorporated, if desired.

In another embodiment the hardenable material can be or comprise a free-radically polymerizable material, including ethylenically unsaturated monomer, monomers or oligomers or polymers. The free-radically polymerizable material or mixtures thereof might be present alone (i.e. without cationically polymerizable material) or in addition thereto.

Suitable free-radically polymerizable materials contain at least one ethylenically unsaturated bond, and are capable of undergoing addition polymerization. Such free-radically polymerizable materials include mono-, di- or poly-acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyldimethylmethane, bis[1-(3-acryloxy-2-hydroxy)]-p-propoxyphenyldimethylmethane, and trishydroxyethyl-isocyanurate trimethacrylate; the bis-acrylates and bis-methacrylates of polyethylene glycols of molecular weight 200-500, copolymerizable mixtures of acrylated monomers such as those in U.S. Pat. No. 4,652,274, and acrylated oligomers such as those of U.S. Pat. No. 4,642,126; and vinyl compounds such as styrene, diallyl phthalate, divinyl succinate, divinyl adipate and divinylphthalate. Mixtures of two or more of these free radically polymerizable materials can be used if desired.

If desired, the polymerizable material(s) may contain both cationically polymerizable and free-radically polymerizable functionalities in a single molecule. These may be obtained, for example, by reacting a di- or poly-epoxide with one or more equivalents of an ethylenically unsaturated carboxylic acid. Examples of such materials include the reaction product of UVR-6105 (available from Union Carbide) or DER 332 (available from Dow Chemical Co.) with one equivalent of methacrylic acid. Commercially available materials having epoxy and free-radically polymerizable functionalities include the "Cyclomer" series, such as Cyclomer M100 or M101, available from Daicel Chemical, Japan.

The polymerizable material(s) can also contain hydroxyl and free-radically polymerizable functionalities in a single molecule. Examples of such materials include hydroxyalkylacrylates and hydroxyalkylmethacrylates such as hydroxyethylacrylate, hydroxyethylmethacrylate; glycerol mono- or di-acrylate and methacrylate; and the like.

The free radically polymerizable material(s) are typically combined with a two-component or binary photoinitiator system.

The hardenable material (cationically curing and/or radically curing material) is typically present in an amount of at least about 0.01 to about 80 wt.-% or at least about 0.1 to about 70 wt.-% or at least about 1 to about 60 wt.-% with respect to the whole composition.

The optional hydroxyl group containing material that may be used in the present invention can be any organic material having hydroxyl functionality of at least 1 or at least 2.

Preferably the hydroxyl group containing material contains two or more primary or secondary aliphatic hydroxyl groups (i.e., the hydroxyl group is bonded directly to a non-aromatic carbon atom). The hydroxyl groups can be terminally situated, or they can be pendent from a polymer or copolymer. The molecular weight of the hydroxyl-containing organic material can vary from very low (e.g., 32) to very high (e.g., one million or more). Suitable hydroxyl-containing materials can have low molecular weights, i.e. from about 32 to 200, intermediate molecular weight, i.e. from about 200 to 10,000, or high molecular weight, i.e. above about 10,000. As used herein, all molecular weights are weight average molecular weights.

The hydroxyl group containing material can optionally contain other functionalities that do not substantially interfere with cationic polymerization at room temperature. Thus, the hydroxyl group containing materials can be nonaromatic in nature or can contain aromatic functionality. The hydroxyl-containing material can optionally contain heteroatoms in the backbone of the molecule, such as nitrogen, oxygen, sulfur, and the like, provided that the ultimate hydroxyl-containing material does not substantially interfere with cationic polymerization at room temperature. The hydroxyl group containing material can, for example, be selected from naturally occurring or synthetically prepared cellulosic materials. Of course, the hydroxyl group containing material is also substantially free of groups that may be thermally or photolytically unstable; that is, the material will not decompose or liberate volatile components at temperatures below about 100° C. or in the presence of actinic light that may be encountered during the desired polymerization conditions for the photocopolymerizable composition.

Representative examples of suitable hydroxyl group containing materials having a hydroxyl functionality of 1 include alkanols, monoalkyl ethers of polyoxyalkyleneglycols, monoalkyl ethers of alkylene-glycols, and others known in the art.

Representative examples of useful monomeric polyhydroxy organic materials include alkylene glycols (e.g., 1,2-ethanediol; 1,3-propanediol; 1,4-butanediol; 1,6-hexanediol; 1,8-octanediol; 2-ethyl-1,6-hexanediol; bis(hydroxymethyl) cyclohexane; 1,18-dihydroxyoctadecane; 3-chloro-1,2-propanediol); polyhydroxyalkanes (e.g., glycerine, tri-methylolethane, pentaerythritol, sorbitol) and other polyhydroxy compounds such as N,N-bis(hydroxyethyl)benzamide; 2-butyne-1,4-diol; 4,4-bis(hydroxymethyl)diphenylsulfone; castor oil; and the like.

Representative examples of useful polymeric hydroxyl group containing materials include polyoxyethylene and polyoxypropylene glycols, and particularly the polyoxyethylene and polyoxypropylene glycol diols and triols having molecular weights from about 200 to about 10,000 corresponding to a hydroxy equivalent weight of 100 to 5000 for the diols or 70 to 3300 for triols; polytetramethylene ether glycols such as polytetrahydrofuran or "poly THF" of varying molecular weight; copolymers of hydroxypropyl and hydroxyethyl acrylates and methacrylates with other free radical-polymerizable monomers such as acrylate esters, vinyl halides, or styrene; copolymers containing pendent hydroxy groups formed by hydrolysis or partial hydrolysis of vinyl acetate copolymers, polyvinylacetal resins containing pendent hydroxyl groups; modified cellulose polymers such as hydroxyethylated and hydroxypropylated cellulose; hydroxy-terminated polyesters; hydroxy-terminated polylactones, and particularly the polycaprolactones; fluorinated polyoxyethylene or polyoxypropylene glycols; and hydroxy-terminated polyalkadienes.

Useful commercially available hydroxyl group containing materials include the "TERATHANE" series of polytetramethylene ether glycols such as "TERATHANE" 650, 1000, 2000 and 2900 (available from du Pont de Nemours, Wilmington, Del.), polytetrahydrofuran with an average molecular weight of 250 (available from Sigma-Aldrich, St. Louis, Mo.), the "PEP" series of polyoxyalkylene tetrols having secondary hydroxy groups such as "PEP" 450, 550 and 650; "BUTVAR" series of polyvinylacetal resins such as "BUTVAR" B-72A, B-73, B-76, B-90 and B-98 (available from Monsanto Chemical Company, St. Louis, Mo.); and the "FORMVAR" series of resins such as 7/70, 12/85, 7/95S, 7/95E, 15/95S and 15/95E (available from Monsanto Chemical Company); the "TONE" series of polycaprolactone polyols such as "TONE" 0200, 0210, 0230,0240, 0300 and 0301 (available from Union Carbide); "PARAPLEX U-148" aliphatic polyester diol (available from Rohm and Haas, Philadelphia, Pa.), the "MULTRON" R series of saturated polyester polyols such as "MULTRON" R-2, R-12A, R-16, R-18, R-38, R-68 and R-74 (available from Mobay Chemical Co.); "KLUCEL E" hydroxypropylated cellulose having an equivalent weight of approximately 100 (available from Hercules Inc.); "Alcohol Soluble Butyrate" cellulose acetate butyrate ester having a hydroxyl equivalent weight of approximately 400 (available from Eastman Kodak Co., Rochester, N.Y.); polyether polyols such as polypropylene glycol diol (e.g., "ARCOL PPG-425", "Arcol PPG-725", "ARCOL PPG-1025", "ARCOL PPG-2025", ARCOL PPG-3025", "ARCOL PPG-4025" from ARCO Chemical Co.); polypropylene glycol triol (e.g., "ARCOL LT-28", "ARCOL LHT-42", "ARCOL LHT 112", "ARCOL LHT 240", "ARCOL LG-56", "ARCOL LG-168", "ARCOL LG-650" from ARCO Chemical Co.); ethylene oxide capped polyoxypropylene triol or diol (e.g., "ARCOL 11-27", "ARCOL 11-34", "ARCOL E-351", "ARCOL E-452", "ARCOL E-785", "ARCOL E-786" from ARCO Chemical Co.); ethoxylated bis-phenol A; propylene oxide or ethylene oxide-based polyols (e.g., "VORANOL" polyether polyols from the Dow Chemical Co.).

The amount of hydroxyl group containing organic material optionally used in the compositions of the invention may vary over broad ranges, depending upon factors such as the compatibility of the hydroxyl-containing material with the resin, the equivalent weight and functionality of the hydroxyl-containing material, the physical properties desired in the final cured composition, the desired speed of photopolymerization, and the like.

Blends of various hydroxyl groups containing materials are also contemplated in this invention. Examples of such blends include two or more molecular weight distributions of hydroxyl-containing compounds, such as low molecular weight (below 200), intermediate molecular weight (about 200 to 10,000) and higher molecular weight (above about 10,000). Alternatively or additionally, the hydroxyl-containing material can contain a blend of hydroxyl-containing materials having different chemical natures, such as aliphatic and aromatic, or functionalities, such as polar and non-polar. As an additional example, one may use mixtures of two or more poly-functional hydroxy materials or one or more mono-functional hydroxy materials with poly-functional hydroxy materials.

The cationically polymerizable resin, optional hydroxyl group(s) containing material(s), and optional free radically polymerizable material(s) are combined with a three-component or ternary photoinitiator system.

The inventive composition may comprise a filler or a filler matrix. The filler matrix can be comprised of one filler or a mixture of different fillers.

The nature of filler of the inventive composition is not particularly limited. The size of the filler particles should be such that a homogeneous mixture with the hardenable component(s) forming the resin matrix can be obtained.

Useful fillers include fumed silica, fillers based on fluoroaluminosilicate glasses, quartz, ground glasses, non-water-soluble fluorides such as $CaF_2$, silica gels such as silicic acid, in particular pyrogenic silicic acid and granulates thereof, cristobalite, calcium silicate, zirconium silicate, zeolites, including the molecular sieves, metal oxide powders, such as aluminium or zinc oxides or their mixed oxides, barium sulphate, yttrium fluoride, calcium carbonate.

The silica is usually dispersed within the resin matrix. The silica particles used in the dental compositions of the invention preferably have an average diameter of less than about 200 nm; more preferably, the particles are less than about 100 nm in average diameter. These measurements are preferably based on a TEM (transmission electron microscopy) method, whereby a population is analyzed to obtain an average particle diameter. A preferred method for measuring the particle diameter can be described is as follows:

Samples approximately 80 nm thick are placed on 200 mesh copper grids with carbon stabilized formvar substrates (SPI Supplies—a division of Structure Probe, Inc., West Chester, Pa.). A transmission electron micrograph (TEM) is taken, using JEOL 200CX (JEOL, Ltd. of Akishima, Japan and sold by JEOL USA, Inc.) at 200 Kv. A population size of about 50-100 particles can be measured and an average diameter is determined.

The average surface area of the silica particles is preferably greater than about 15 $m^2/g$ more preferably greater than about 30 $m^2/g$.

Once dispersed in the resin, the silica particles are in a discrete (individual) and unassociated (i.e. non-agglomerated, non-aggregated) condition. "Agglomerated" as used herein, is descriptive of a weak association of particles usually held together by charge or polarity and can be broken down into smaller entities. "Aggregated," as used herein, is descriptive of a strong association of particles often bound together by, for example, residual chemicals treatment; further breakdown of the aggregates into smaller entities is very difficult to achieve.

The silica particles which can be used in the dental materials of the invention are preferably substantially spherical and substantially non-porous. Although the silica is preferably essentially pure, it may contain small amounts of stabilizing ion such as ammonium and alkaline metal ions.

Suitable fumed silicas include for example, products sold under the tradename AEROSIL series OX-50, -130, -150, and -200 available from Degussa AG, (Hanau, Germany), and CAB-O-SIL M5 available from Cabot Corp (Tuscola, Ill.).

Useful fluoroaluminosilicate glasses include silanol treated fluoroaluminosilicate glass fillers, as described in U.S. Pat. No. 5,332,429, the disclosure of which is expressly incorporated by reference herein. For example, a fluoride releasing glass may be added to the dental composition to provide the benefit of long-term release of fluoride in use, for example in the oral cavity.

Optionally, a heavy metal oxide can be included in the dental materials of the invention to provide a radiopaque dental material. It is preferred that the heavy metal oxide be present in an amount effective to impart radiopacity. As used herein, "radiopacity" describes the ability of a hardened dental material to be distinguished from tooth structure using standard dental X-ray equipment in the conventional manner. Radiopacity in a dental material is advantageous in certain instances where X-rays are used to diagnose a dental condition. For example, a radiopaque material would allow the detection of secondary caries that may have formed in the tooth tissue surrounding a filling. The desired degree of radiopacity can be varied, depending upon the particular application and the expectations of the practitioner evaluating the X-ray film.

Oxides of heavy metals having an atomic number greater than about 28 can be preferred. The heavy metal oxide should be chosen such that undesirable colors or shading are not imparted to the hardened resin in which it is dispersed. For example, iron and cobalt would not be favoured, as they impart dark and contrasting colors to the neutral tooth color of the dental material. More preferably, the heavy metal oxide is an oxide of metals having an atomic number greater than 30. Suitable metal oxides are the oxides of yttrium, strontium, barium, zirconium, hafnium, niobium, tantalum, tungsten, bismuth, molybdenum, tin, zinc, lanthanide elements (i.e. elements having atomic numbers ranging from 57 to 71, inclusive), cerium and combinations thereof. Most preferably, the oxides of heavy metals having an atomic number greater than 30, but less than 72 are optionally included in the materials of the invention. Particularly preferred radiopacifying metal oxides include lanthanum oxide, zinc oxide, tin oxide, zirconium oxide, yttrium oxide, ytterbium oxide, barium oxide, strontium oxide, cerium oxide, and combinations thereof. The heavy metal oxide particles may be aggregated. If so, it is preferred that the aggregated particles are less than about 200 nm, and more preferably are less than about 90 nm in average diameter.

In a preferred embodiment the filler matrix comprises a nano-sized filler including nano-sized silica.

Preferred nano-sized silicas are commercially available from Nalco Chemical Co. (Naperville, Ill.) under the product designation NALCO COLLOIDAL SILICAS. For example, preferred silica particles can be obtained from using NALCO products 1040, 1042, 1050, 1060, 2327 and 2329. In a preferred embodiment where the hardenable resin employs a cationic initiation system, the starting silica is preferably acidic (such as Nalco 1042).

Surface-treating the nano-sized silica particles before loading into the dental material can provide a stable dispersion in the resin. "Stable", as used herein, means a dental material in which the particles do not agglomerate after standing for a period of time, such as about 24 hours, under standard ambient conditions, e.g. room temperature (about 20 to about 22° C.), atmospheric pressure, and no extreme electromagnetic forces. Preferably, the surface-treatment stabilizes the nano-sized particles so that the particles will be well dispersed in the hardenable resin and results in a substantially homogeneous composition. Furthermore, it is preferred that the silica be modified over at least a portion of its surface with a surface treatment agent so that the stabilized particle can copolymerize or otherwise react with the hardenable resin during curing.

The silica particles can be treated with a resin-compatibilizing surface treatment agent. Particularly preferred surface treatment or surface modifying agents include silane treatment agents capable of polymerizing with a resin. Preferred silane treatment agent include γ-methacryloxylpropyltrimethoxysilane, available commercially under the trade designation A-174, available commercially from Witco OSi Specialties (Danbury, Conn.) and γ-glycidoxypropyltrimethoxy silane, a product available under the trade designation G6720, available from United Chemical Technologies (Bristol, Pa.).

Alternatively a combination of surface modifying agents can be useful, wherein at least one of the agents has a functional group co-polymerizable with a hardenable resin. For example, the polymerizing group can be ethylenically unsaturated or a cyclic function subject to ring opening polymerization. An ethylenically unsaturated polymerizing group can be, for example, an acrylate or methacrylate, or vinyl group. A cyclic functional group subject to ring opening polymerization generally contains a heteroatom such as oxygen, sulfur or nitrogen, and preferably is a 3-membered ring containing oxygen such as an epoxide. Other surface modifying agents which do not generally react with hardenable resins can be included to enhance dispersibility or rheological properties. Examples of silane of this type include, for example, alkyl or aryl polyethers, alkyl, hydroxy alkyl, hydroxy aryl, or amino alkyl functional silanes.

Upon surface treating the silica particles, they can then be combined with an appropriate hardenable resin to form a dental composition of the invention.

The filler matrix can comprise at least about 25 wt.-% or at least about 30 wt.-% or at least about 40 wt.-% or at least about 50 wt.-% of the whole composition.

The amount of filler to be used in the filler matrix usually depends on the purpose for which the composition should be used.

The filler matrix can comprise up to about 90 wt.-% or up to about 85 wt.-% or up to about 80 wt.-% of the whole composition.

Temporary crown and bridge materials (as an example for a dental composition) usually do not contain a high amount of fillers. With respect to these compositions, the filler content usually is in a range of about 30 to about 60 wt.-% with respect to the whole composition.

In dental filling materials (as another example for a dental composition; sometimes also referred to as dental composite materials), which typically contain a higher amount of fillers compared to temporary crown and bridge materials, the filler content is usually in a range of about 60 to about 85 wt.-% with respect to the whole composition.

Cationically polymerizable compositions of the invention can be prepared with refractive indices which approach or approximate the refractive indices of fillers such as quartz (refractive index 1.55), submicron silica (refractive index 1.46), and 5.5:1 mole ratio $SiO:ZrO$, non-vitreous microparticles (refractive index 1.54). In this way, the appearance of the dental material can, if desired, be made to closely approximate the appearance of natural dentition.

The compositions of the invention can also contain suitable adjuvants such as accelerators, inhibitors or retarders, absorbers, stabilizers, pigments, dyes, viscosity modifiers, surface tension depressants and wetting aids, antioxidants, and other ingredients well known to those skilled in the art.

The amounts and types of each ingredient in the composition should be adjusted to provide the desired physical and handling properties before and after polymerization. For example, the polymerization rate, polymerization stability, fluidity, compressive strength, tensile strength and durability of the dental material typically are adjusted in part by altering the types and amounts of polymerization initiator(s) and, if present, the loading and particle size distribution of filler(s). Such adjustments typically are carried out empirically based on experience with dental materials of the prior art.

Typical adjuvants include pigments, colorants and/or dyes. Examples include titanium dioxide or zinc sulphide (lithopones), red iron oxide 3395, Bayferrox 920 Z Yellow, Neazopon Blue 807 (copper phthalocyanine-based dye) or Helio Fast Yellow ER. These additives may be used for individual coloring of the dental compositions.

Further additives, which can be added, include stabilizers, especially free radical scavengers such as substituted and/or unsubstituted hydroxyaromatics (e.g. butylated hydroxytoluene (BHT), hydroquinone, hydroquinone monomethyl ether (MEHQ), 3,5-di-tert-butyl-4-hydroxyanisole(2,6-di-tert-butyl-4-ethoxyphenol), 2,6-di-tert-butyl-4-(dimethylamino) methylphenol or 2,5-di-tert-butyl hydroquinone, 2-(2'-hydroxy-5'-methylphenyl)-2H-benzotriazole, 2-(2'-hydroxy-5'-t-octylphenyl)-2H-benzotriazole, 2-hydroxy-4-methoxybenzophenone (UV-9), 2-(2'-hydroxy-4',6'-di-tert-pentylphenyl)-2H-benzotriazole, 2-hydroxy-4-n-octoxybenzophenone, 2-(2'-hydroxy-5'-methacryloxyethylphenyl)-2H-benzotriazole, phenothiazine, and HALS (hindered amine light stabilizers). Such adjuvants may optionally comprise reactive functionality so that they will be copolymerized with the resin.

There is no absolute need for these adjuvants to be present, so adjuvants might not be present at all. However, if they are present they are typically present in an amount of at least about 0.01 wt.-% or at least about 0.5 wt.-% or at least about 1 wt.-% with respect to the whole composition.

The adjuvants can be present in an amount up to about 25 wt.-% or up to about 20 wt.-% or up to about 15 wt.-% with respect to the whole composition.

The curable composition of the invention can be obtained by combining (including mixing and kneading) the individual components of the composition, preferably under "safe light" conditions.

Suitable inert solvents may be employed if desired when providing the mixture. Any solvent may be used which does not react appreciably with the components of the inventive compositions. Examples of suitable solvents include acetone, dichloromethane, acetonitrile and lactones. A liquid material to be polymerized may be used as a solvent for another liquid or solid material to be polymerized. Solventless compositions can be prepared by simply dissolving the iodonium complex salt, sensitizer, and electron donor in the cationically polymerizable resin, with or without the use of mild heating to facilitate dissolution.

The individual components of the initiator system are typically provided in effective amounts (i.e., amounts effective to yield e.g. a photoinitiator system that can initiate photopolymerization of the cationically polymerizable resin or, more preferably, that can accelerate the rate of polymerization).

According to another embodiment of the invention, the hardenable composition may comprise
  the initiator system in an amount of at least about 0.1 wt.-% or at least about 0.3 wt.-% or at least about 0.7 wt.-% or at least about 1 wt.-% or at least about 2 wt.-%,
  the hardenable material in an amount of at least about 0.01 wt.-% or at least about 1 wt.-% or at least about 10 wt.-% or at least about 20 wt.-%,
  optionally filler(s) in an amount of utmost about 90 wt.-% or of utmost about 80 wt.-% or of utmost about 60 wt.-% or of utmost about 30 wt.-%,
  optionally hydroxyl group containing material(s) in an amount of utmost about 5 wt.-% or of utmost about 3 wt.-% or of utmost about 1 wt.-% and
  optionally adjuvants in an amount of utmost about 25 wt.-% or of utmost about 20 wt.-% or of utmost about 15 wt.-% or of utmost about 10 wt.-%,
wt.-% with respect to the whole composition.

The inventive dental composition is typically stored in a container until use. Depending on the initiator system chosen, various containers can be suitable.

If the dental composition is provided as a one-component system, it can be stored in a container having only one chamber such as a compule. The compule has typically a cylindrical housing with a front and a rear end and a nozzle. The rear end of the housing is usually sealed with a movable piston. Typically, the dental composition is dispensed out of the compule or container using an applier having a movable plunger (e.g. an application device having the shape of a caulk gun). Examples of suitable compules or containers are described in U.S. Pat. No. 5,624,260, EP 1 340 472 A1, US 2007/0172789 A1, U.S. Pat. No. 5,893,714 and U.S. Pat. No. 5,865,803, the content of which with regard to the description of compules or containers is herewith incorporated by reference.

Alternatively, if the dental composition is provided as a two-component system, it can be stored in a dual-chamber container or cartridge and is mixed before use.

Cartridges which can be used are described e.g. in US 2007/0090079 or U.S. Pat. No. 5,918,772, the disclosure of which is incorporated by reference. Cartridges which can be used are commercially available from SulzerMixpac AG (Switzerland).

Static mixing tips which can be used are described e.g. in US 2006/0187752 or in U.S. Pat. No. 5,944,419, the disclosure of which is incorporated by reference. Mixing tips which can be used are commercially available from SulzerMixpac AG (Switzerland).

Thus, another embodiment of the invention is directed to the hardenable composition or a kit of parts stored in a container, the container comprising a housing with a front end with a nozzle and a rear end and at least one piston movable in the housing.

The present invention provides a system for hardening resins, including cationically and/or radically polymerizable resins, in an acceptable time frame, e.g., less than about 120 seconds (s) or less than about 100 s or less than about 60 s, and to a sufficient depth using visible light source equipment already available in the dental office or electronics fabrication facilities.

The compositions of the invention are particularly well adapted for use as a wide variety of dental materials, which may be filled or unfilled. Such dental materials include direct aesthetic restorative materials (e.g., anterior and posterior restoratives), prostheses, adhesives and primers for oral hard tissues, sealants, veneers, cavity liners, orthodontic bracket adhesives for use with any type of bracket (such as metal, plastic and ceramic), crown and bridge cements, artificial crowns, artificial teeth, dentures, and the like. These dental materials are used in the mouth and are disposed adjacent to natural teeth. The phrase "disposed adjacent to" as used herein refers to the placing of a dental material in temporary or permanent bonding (e.g., adhesive) or touching (e.g., occlusal or proximal) contact with a natural tooth. The term "composite" as used herein in the context of a dental material refers to a filled dental material. The term "restorative" as used herein refers to a dental composite that is polymerized after it is disposed adjacent to a tooth. The term "prosthesis" as used herein refers to a composite that is shaped and polymerized for its final use (e.g., as a crown, bridge, veneer, inlay, onlay or the like) before it is disposed adjacent to a tooth. The term "sealant" as used herein refers to a lightly filled dental composite or to an unfilled dental material that is cured after it is disposed adjacent to a tooth.

When the dental material is applied to a tooth, the tooth can optionally be pre-treated with a primer such as dentin or enamel adhesive by methods known to those skilled in the art.

The invention is also directed to the use of the inventive photoinitiator system for the production of a dental composition or material, the process of using comprising the steps of:

a) placing the dental composition comprising the photoinitiator system in contact with a tooth, b) hardening the composition.

In addition to the use in dental applications, the useful combination of high cure speed, high cure depth, temperature insensitivity and low colour formation achievable with this invention in low-stress epoxy resins could find use in other applications.

These could include hardcoats for a variety of substrates including various metals, glasses, plastics, papers, wood and the like. Other potential applications include graphic arts imaging (including curable inks, silverless imaging layers, an imaging layer on a projection plate, an imaging layer on a laser plate), photoresists, solder masks, electronic coatings, photocurable adhesives (including orthodontics), non-dental photocurable composites (including automotive parts or repair), a hard coat layer on an optical lens, or a coating on an optical fibre.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

EXAMPLES

Unless otherwise indicated, all parts and percentages are on a weight basis, all water is deionized water, and all molecular weights are weight average molecular weight. Moreover, unless otherwise indicated all Experiments were conducted at ambient conditions (23° C.; 1013 mbar).

TABLE 1

Components/Abbreviations

| | | Description and Source of Material |
|---|---|---|
| a | Methylbis[2-(7-oxabicyclo-[4.1.0]hept-3-yl)ethyl]phenyl silane | Silorane resin; as described for "Monomer Composition 2" in U.S. patent application No. 2003/0035899 (Klettke et al.) |
| b | 1,3,5,7-Tetrakis(1,2-ethanediyl-3,4-epoxycyclohexyl)-1,3,5,7-tetramethylcyclotetrasiloxane | Silorane resin; as described for "Monomer Composition 2" in U.S. patent application No. 2003/0035899 (Klettke et al.) |
| c | CQ | Camphorquinone (Sigma-Aldrich) |
| d | EDMAB | Ethyl 4-dimethylaminobenzoat |
| e | DBPMA | N,N-Di(4-tert-butylphenyl)-N-methylamine |
| f | DPMA | N,N-Diphenyl-N-methylamine |

TABLE 1-continued

Components/Abbreviations

Description and Source of Material

| | | |
|---|---|---|
| g | DAMA | N,N-Di(3-anisyl)-N-methylamine |
| h | APMA | N-(3-Anisyl)-N-phenyl-N-methylamine |
| i | TPA | N,N,N-Triphenylamine (Sigma-Aldrich) |
| j | TTA | N,N,N-Tri(4-tolyl)amine (Sigma-Aldrich) |
| k | MTPA | 3-Methoxy-N,N,N-triphenylamine (Sigma-Aldrich) |
| l | Anthracene | (Sigma-Aldrich) |
| m | EDMO | 2-Ethyl-9,10-dimethoxyanthracene (Sigma-Aldrich) |

TABLE 1-continued

Components/Abbreviations

| | | Description and Source of Material |
|---|---|---|
| n | Rhodia Silbione PI | (4-Cumyl)-(4-tolyl)iodonium Tetrakis(2,3,4,5,6-pentafluorophenyl)borate (Rhodia) |
| o | Filler | Silane-treated quartz filler [prepared by silane treating quartz (Quarzwerke GmbH, Germany) with 3-glycidyloxypropyl-trimethoxysilane (ABCR GmbH, Karlsruhe, Germany) at a level of 5% by weight using standard silane-treatment procedures.] |
| p | Radiopacifier | Yttriumtrifluoride (YF$_3$) |
| q | pTHF 250 | Polytetrahydrofuran, mean molecular weight 250 (Sigma-Aldrich) |
| r | Bis-GMA | 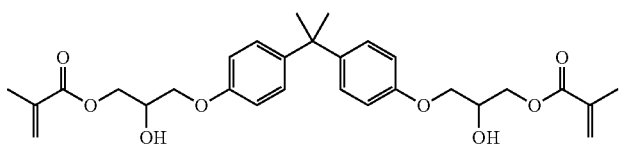 |
| s | TEGDMA | Triethyleneglycol dimethacrylate |
| t | Filler | spray dried zirconia silica filler, <1 μm, surface treated; as described in sections [0083] and [0084] of U.S. 2004/0082683. |

Measurements

Depth of Cure (DOC)

DOC was evaluated according to ISO 4049 using either a metal mould or a Delrin™ mould and is given in mm.

Depth of Cure Test Method A

Depth of cure (i.e., cure depth) was analyzed according to ISO 4049 by packing a paste sample into a cylindrical metal curing mould (8 mm deep, 4 mm diameter) and curing the sample for 40 seconds with an ELIPAR™ Trilight Standard (800 mW/cm$^2$) (3M ESPE Company). The cured sample was removed from the mould and uncured paste was scraped off of the sample with a plastic applicator after less than about one minute of curing. Results were reported as the average of three replicates.

Depth of Cure Test Method B

Depth of cure (i.e., cure depth) was analyzed as described in the Depth of Cure Test Method A according to ISO 4049, except that the curing mould was a 12 mm deep Delrin™ mold.

Fluorescence

The fluorescence was evaluated as follows:

A test sample paste was pressed into a 1.5 mm thick mould (15 mm diameter) and irradiated for 20 seconds (s) with a broad spectrum white light and then for 4*50 seconds with a 800 mW/cm$^2$ curing light (ELIPAR™ Trilight Standard, 3M ESPE Company) in five partially overlapping curing areas with respect to the light tip outlet diameter. These cured disks were analyzed on a SPACTRAmax GEMINI XS (Molecular Devices, Sunnyvale Calif.). Using a 24 well plate the disks were irradiated with monochromatic radiation of 355 nm wavelength at room temperature. The corresponding fluorescence emission spectra were recorded using the SOFTmax PRO software program (version Enterprise 4.8, Molecular Devices) in the wavelength range of 370 nm to 650 nm in steps of 10 nm each in the presence of the disk containing the reference compound as internal relative standard. The Absolute Fluorescence Emission Intensity is given in Relative Fluorescence Units (RFU). The Fluorescence Emission Wavelengths of the corresponding Maximum Fluorescence Emissions were determined in nm within the recorded range of 370 nm to 650 nm.

General Procedure A:

All operations were performed under a protective atmosphere of dry nitrogen.

N,N-Di(4-tert-butylphenyl)-N-methylamine (DBPMA)

12.5 g (65.6 mmol) of N,N-Diphenyl-N-methylamine (Aldrich, 96%) were mixed with 74.8 g (656 mmol) of trifluoroacetic acid (99%). After addition of 48.7 g (656 mmol) of tert-butanole (99%) the resulting mixture was heated to reflux for 16 hours. At room temperature the reaction mixture was poured into 1500 ml of water. 42.4 g of sodium carbonate were added carefully in portions with stirring. After phase separation the organic layer was washed three times with water. The collected aqueous phases were extracted twice with diethylether and then the collected organic phases are dried with anhydrous sodium sulfate. After distillation of the solvent in vacuo the crude residue was crystallized from methanole. The yellowish precipitate (6.40 g, 34.0% yield) was separated via filtration and then crystallized a second time from methanole. After drying N,N-Di(4-tert-butylphenyl)-N-methylamine (DBPMA) was isolated as colorless solid in 17.0% yield (3.20 g).

N,N-Diphenyl-N-methylamine (DPMA)

Commercially available DPMA (Aldrich) was further purified via fractionated distillation in vacuo and stored under a protective argon atmosphere until usage.

N,N-Di(3-Anisyl)-N-methylamine (DAMA)

10.0 g of N,N-Di(3-Anisyl)amine were dissolved 436 ml of anhydrous THF. 14.0 g of paraformaldehyde were added with stirring followed by 8.20 g of sodium borohydride. 190 ml of trifluoro acetic acid were added during 120 min and after completion of the addition the reaction mixture was stirred at room temperature over night. The reaction mixture was poured into 654 ml of an ice cubes containing 25.0%-weight solution of sodium hydroxide in water. After addition of 654 ml of a saturated aqueous solution of sodium chloride it was extracted three times with each 650 ml of dichloromethane and the combined organic extracts were dried with anhydrous sodium sulfate. After filtration the solvent was removed in vacuo and the crude product purified by fractionated distillation in vacuo. At a temperature of 125-135° C./0.04 mbar 8.60 g (80.4%) of DAMA are collected as yellow liquid.

N-(3-Anisyl)-N-phenyl-N-methylamine (APMA)

5.15 g of N-(3-Anisyl)-N-phenyl-amine were dissolved in 25.0 ml of anhydrous diethylether. 11.0 g of a 2.50 M solution of n-butyl lithium in n-hexane was added with stirring. After completion of the addition the reaction mixture was heated to reflux for 30 min 3.90 g of iodomethane are added and the reaction mixture was heated to reflux for additional 4 hours. After extraction with 2.00 N sodium hydroxide solution (three times) the organic layer was dried with anhydrous sodium sulfate. After filtration the solvent was removed in vacuo and the crude product purified by fractionated distillation in vacuo. At a temperature of 70-90° C./0.01 mbar 2.40 g (45.0%) of APMA was collected as yellow liquid.

General Procedure B

With magnetic stirring and under the exclusion of light the initiator system components were dissolved within the monomers at temperatures not above 50° C. (depending on the intrinsic viscosity of the used monomers). The obtained composition was then light cured using an 800 mW halogen curing light (3M ESPE Elipar™ Trilight) and tested according to the corresponding measurements listed above.

TABLE 2

Cationically Curing Compositions[1]

| | A[2] | B[2] | C[3] | D[4] | E[5] | F[5] | G[4] | H[4] | I[4] | J[4] | K[4] |
|---|---|---|---|---|---|---|---|---|---|---|---|
| a | 11.1 | 11.1 | 11.1 | 11.4 | 11.3 | 11.3 | 11.3 | 11.3 | 11.3 | 11.3 | 11.3 |
| b | 11.1 | 11.1 | 11.1 | 11.3 | 11.3 | 11.3 | 11.3 | 11.3 | 11.3 | 11.3 | 11.3 |
| c | 0.12 | 0.12 | 0.12 | 0.07 | 0.07 | 0.07 | 0.07 | 0.07 | 0.07 | 0.07 | 0.07 |
| d | | 0.05 | | | | | | | | | |
| e | | | 0.12 | | | 0.11 | | | | | |
| f | | | | | | 0.07 | | | | | |
| g | | | | | | | 0.09 | | | | |
| h | | | | | | | | 0.08 | | | |
| i | | | | | | | | | 0.09 | | |
| j | | | | | | | | | | 0.11 | |
| k | | | | | | | | | | | 0.10 |
| l | 0.02 | | | | | | | | | | |
| m | 0.01 | | | 0.02 | | | | | | | |
| n | 0.71 | 0.71 | 0.70 | 0.35 | 0.35 | 0.35 | 0.35 | 0.35 | 0.35 | 0.35 | 0.35 |
| o | 64.7 | 64.7 | 64.7 | 65.0 | 65.0 | 65.0 | 65.0 | 65.0 | 65.0 | 65.0 | 65.0 |
| p | 11.5 | 11.5 | 11.5 | 11.5 | 11.5 | 11.5 | 11.5 | 11.5 | 11.5 | 11.5 | 11.5 |
| q | 0.71 | 0.71 | 0.70 | 0.35 | 0.35 | 0.35 | 0.35 | 0.35 | 0.35 | 0.35 | 0.35 |
| CS[6] | 329 ± 24.0 | 346 ± 17.0 | 346 ± 22.0 | n.a. | 331.00 ± 23.0 | 334 ± 19.0 | n.a. | n.a. | 336 6.00± | 310 ± 12.0 | n.a. |
| FS[7] | 126 ± 12.0 | 116 ± 7.00 | 123 ± 5.00 | n.a. | 105.00 ± 13.0 | 110 ± 21.0 | n.a. | n.a. | 97.0 ± 13.0 | 103 ± 4.00 | n.a. |
| E-M.[8] | 10.1 ± 0.30 | 8.80 ± 0.30 | 10.0 ± 0.30 | n.a. | 8.50 ± 0.30 | 9.70 ± 0.50 | n.a. | n.a. | 9.10 ± 0.40 | 8.40 ± 0.40 | n.a. |
| DOC[9] | 2.30 | 2.63 | 2.20 | 2.37 | 2.55 | 2.56 | 1.96 | 2.14 | n.a. | n.a. | n.a. |
| DOC[10] | 3.97 | 3.98 | 3.61 | 3.87 | 4.61 | 4.04 | 3.13 | 3.49 | 2.67 | 2.16 | 2.94 |
| ACTA[11] | 1.80 ± 0.19 | 2.10 ± 0.31 | 1.80 ± 0.19 | n.a. | n.a. | n.a. | n.a. | n.a. | n.a. | n.a. | n.a. |
| Watts[12] | 0.82 ± 0.03 | 1.15 ± 0.05 | 0.82 ± 0.06 | n.a. | n.a. | n.a. | n.a. | n.a. | n.a. | n.a. | n.a. |
| $\lambda_{max, Em.}$[13] | 430 | 420 | 420 | 450 | 400 | 420 | 390 | 420 | 390 | 390 | 450 |
| Int.$_{Em.}$[14] | 24.0 | 9.43 | 9.22 | 100 | 49.8 | 57.8 | 22.3 | 34.8 | 93.9 | 88.7 | 26.4 |

[1]Amounts of ingredients are given in %-weight.
[2]Kneaded paste
[3]Kneaded paste
[4]Speed mixed paste
[5]Speed mixed paste
[6]Compressive Strength in MPa according to ISO 9917 using cubic specimen (dimensions 3 mm × 3 mm × 5 mm).
[7]Flexural Strength in MPa according to ISO 4049.
[8]E-Modulus in GPa according to ISO 4049.
[9]Depth of cure given in mm, metal mold, according to ISO 4049.
[10]Depth of cure given in mm, delrin mold, according to ISO 4049.
[11]Two Body Wear Resistance according to ACTA relative to 3M ESPE Filtek Z250.
[12]Bonded Disk Shrinkage-Strain in % according to the Watts protocol.
[13]Fluorescence Emission Wavelength of the Maximum Fluorescence Emission given in nm.
[14]Relative Fluorescence Emission Intensity at the Maximum Fluorescence Emission Wavelength given in rel.-% compared to the fluorescence emission intensity of the reference compound EDMO showing an Absolute Fluorescence Emission Intensity of 48800 RFU (Relative Fluorescence Units) at its Maximum Fluorescence Emission Wavelength of 450 nm.
n.a.: not analysed For cationically curing compositions it has been found that in contrast to aniline derivatives as well as in contrast to N,N,N-triphenylamine derivatives, as well as in contrast to polycyclic aromatic donors the inventive diaryl alkyl amine components enables the provision of compositions showing a good combination of mechanical (e.g. depth of cure, wear resistance and/or shrinkage) and aesthetic properties (e.g. less fluorescence).

TABLE 3

Radically Curing Compositions[1]

| | L[2] | M[3] |
|---|---|---|
| c | 0.06 | 0.06 |
| d | 0.17 | |
| e | | 0.26 |
| r | 8.34 | 8.29 |
| s | 8.34 | 8.29 |
| t | 83.1 | 83.1 |
| CS[6] | 461 ± 53.0 | 468 ± 18.0 |
| FS[7] | 139 ± 16.0 | 126 ± 29.0 |
| E-M.[8] | 14.1 ± 0.40 | 13.7 ± 0.60 |
| Watts[12] | 2.32 ± 0.01 | 2.25 ± 0.01 |
| $\lambda_{max,Em.}$[13] | 380 | 440 |
| Int.$_{Em.}$[14] | 71.3 | 8.40 |

For radically curing compositions it has been found that the inventive diaryl alkyl amine components enables the provision of compositions showing a good combination of mechanical (e.g. compressive strength, flexural strength, E-Modulus and/or shrinkage) and aesthetic properties (e.g. less fluorescence).

The invention claimed is:

1. Initiator system comprising
a diarylalkylamine compound having the following structure:
Ar$^1$Ar$^2$RN,
with Ar$^1$ and Ar$^2$ being independently selected from phenyl or alkyl substituted phenyl, R being an alkyl group wherein one or more H atoms can be substituted by halogen and N being nitrogen; and
a sensitizing agent.

2. The initiator system according to claim 1, wherein the diarylalkylamine compound is characterized by at least one of the following features:
Molecular mass being in a range of about 150 to about 400,
pK$_b$-value greater than about 8,
Oxidation Potential less than about 1.35 volts when measured using a saturated calomel electrode,
the diaryl substituents of the diarylalkylamine compound not containing alkoxy substituents,
the diarylalkylamine compound comprising at least one alkyl group on the aryl substituent(s).

3. The initiator system according to claim 1, wherein the diarylalkylamine compound is selected from the group of

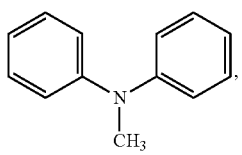

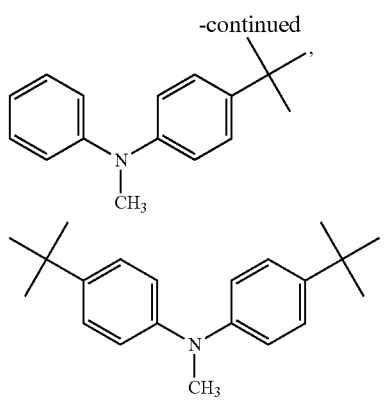

and combinations thereof.

4. The initiator system according to claim 1 further comprising an iodonium salt.

5. The initiator system according to claim 4, wherein the iodonium salt is selected from diaryliodonium hexafluorophosphate, diaryliodonium hexafluoroantimonate, diaryliodonium tetrakis(pentafluorophenyl)borate, 4-octyloxyphenyl phenyliodonium hexafluoroantimonate, 4-(2-hydroxytetradecyloxyphenyl)phenyliodonium hexafluoroantimonate, 4-(1-methylethyl)phenyl 4-methylphenyliodonium tetrakis(pentafluorophenyl)borate, and combinations thereof.

6. The initiator system according to claim 1, wherein the sensitizing agent comprises compounds from the following categories: ketone, coumarin, xanthene, fluorone, fluorescein, aminoketone, and aminostyryl ketone.

7. Hardenable composition comprising
an initiator system, the initiator system comprising:
a diarylalkylamine compound having the following structure:
Ar$^1$Ar$^2$RN,
with Ar$^1$ and Ar$^2$ being independently selected from phenyl or alkyl substituted phenyl, R being an alkyl group wherein one or more H atoms can be substituted by halogen and N being nitrogen; and
a sensitizing agent and
a hardenable material.

8. A hardenable composition according to claim 7, wherein the composition is a radically curing composition.

9. The hardenable composition according to claim 7 being a cationically curing composition or a radically curing composition or a mixture thereof, with the proviso that if the hardenable composition is a cationically curing composition, the initiator system comprises in addition an iodonium salt as described in claim 4.

10. The hardenable composition according to claim 7, wherein the hardenable material is selected from epoxy, oxetane, vinyl ether, spiro-orthocarbonate resin(s) and combinations thereof and/or free-radically polymerizable resin(s).

11. The hardenable composition according to claim 7 further comprising at least one of the following components:
filler,
a hydroxyl group containing material, or
adjuvant(s).

12. The hardenable composition according to claim 7, wherein the hardenable composition has at least one of the following parameters:
Compressive Strength determined according to ISO 9917 using cubic specimen (dimensions 3 mm×3 mm×5 mm): at least about 310 MPa;

Flexural Strength determined according to ISO 4049: at least about 100 MPa;

E-Modulus determined according to ISO 4049: at least about 8 GPa; or

Depth of Cure determined according to ISO 4049: at least about 2.10 mm (metal mold) or at least about 3.50 mm (delrin mold).

13. A process for initiating the hardening process of a hardenable composition, the process comprising:

combining an initiator system according to claim 1 with a hardenable composition, the hardenable composition selected from cationically curing composition(s), radically curing composition(s), or mixtures thereof.

14. The process according to claim 13, wherein the hardenable composition is selected from a photopolymerizable adhesive, a curable ink imaging layer, a silverless imaging layer, an imaging layer on a projection plate, an imaging layer on a laser plate, or a dental material.

15. A process for producing artificial crowns, anterior or posterior fillings, casting materials, cavity liners, cements, coating compositions, mill blanks, orthodontic devices, restoratives, prostheses or sealants, dental adhesives or dental composites, the process comprising:

placing a hardenable composition according to claim 7 into contact with a tooth; and hardening the hardenable composition.

* * * * *

UNITED STATES PATENT AND TRADEMARK OFFICE
CERTIFICATE OF CORRECTION

PATENT NO.        : 8,314,162 B2
APPLICATION NO.   : 12/996906
DATED             : November 20, 2012
INVENTOR(S)       : Bettina Hailand It is certified that error appears in the above-identified patent and that said Letters Patent is hereby corrected as shown below:

Column 1
Lines 37-38        Delete "4-dimethylaminobenzoat" and insert
                   -- 4-dimethylaminobenzoate --, therefor.

Column 2
Lines 21-22        Delete "initiatorsystem" and insert -- initiator system --, therefor.
Line 26            Delete "initiatorsystems" and insert -- initiator systems --, therefor.
Lines 29-30        Delete "initiatorsystem" and insert -- initiator system --, therefor.

Column 3
Line 4             Delete "i.a." and insert -- i.e. --, therefor.

Column 6
Line 24            Delete "substitutent(s)" and insert -- substituent(s) --, therefor.
Line 27            Delete "substitutent(s)" and insert -- substituent(s) --, therefor.
Line 32            Delete "substitutent(s)" and insert -- substituent(s) --, therefor.

Column 12
Line 12            Delete "Particulary" and insert -- Particularly --, therefor.

Column 19
Lines 17-18        Delete "Neazopon" and insert -- Neozapon --, therefor.

Column 22 (TABLE 1)
Line 6 (Approx.)   Delete "resin;" and insert -- resin --, therefor.
Line 10 (Approx.)  Delete "4-dimethylaminobenzoat" and insert
                   -- 4-dimethylaminobenzoate --, therefor.

Signed and Sealed this
Second Day of April, 2013

Teresa Stanek Rea
*Acting Director of the United States Patent and Trademark Office*

Column 25 (TABLE 1-continued)
Line 4 (Approx.)   Delete "pentafluorophcnyl" and insert -- pentafluorophenyl --, therefor.
Line 6 (Approx.)   Delete "(Quarzwerkc" and insert -- (Quarzwerke --, therefor.

Column 25
Line 54            Delete "SPACTRAmax" and insert -- SPECTRAmax --, therefor.

Column 26
Line 37 (Approx.)  Delete "tert-butanole" and insert -- tert-butanol --, therefor.
Line 46            Delete "methanole." and insert -- methanol. --, therefor.
Line 48            Delete "methanole." and insert -- methanol. --, therefor.